Figure 1:
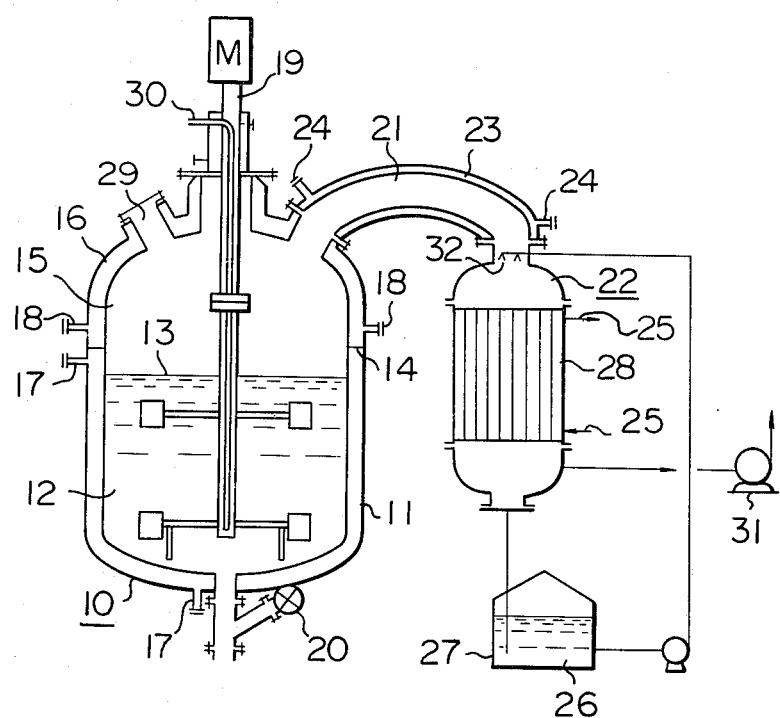

United States Patent [19]

Nezu et al.

[11] 4,369,097

[45] Jan. 18, 1983

[54] METHOD AND APPARATUS OF DISTILLATION FOR READILY POLYMERIZABLE LIQUID

[75] Inventors: Satoshi Nezu, Oisomachi; Keijin Goto; Seisuke Yano, both of Yokohama, all of Japan

[73] Assignee: Asahi Kasei Kogyo Kabushiki Kaisha, Osaka, Japan

[21] Appl. No.: 296,046

[22] Filed: Aug. 25, 1981

[30] Foreign Application Priority Data

Aug. 29, 1980 [JP] Japan .................................. 55-118418
Aug. 29, 1980 [JP] Japan .................................. 55-118419

[51] Int. Cl.³ ............................................. B01D 3/02
[52] U.S. Cl. ........................................ 203/100; 203/8; 203/42; 202/184; 202/185 A; 560/218
[58] Field of Search ....................... 203/6-9, 203/91, 99, 100, 42, 87; 202/205, 185 A, 182-184, 235, 202; 585/832, 950; 560/4, 218; 159/2 R, 23; 196/138; 34/73

[56] References Cited

U.S. PATENT DOCUMENTS

| | | | |
|---|---|---|---|
| 1,202,969 | 10/1916 | Cornell | 159/23 |
| 2,407,616 | 9/1946 | Phelps et al. | 203/100 |
| 2,491,732 | 12/1949 | Hawkinson et al. | 203/6 |
| 2,515,013 | 7/1950 | Kruhmin | 203/100 |
| 2,702,268 | 2/1955 | Egger et al. | 203/100 |
| 2,996,351 | 8/1961 | Stobe | 203/6 |
| 3,020,214 | 2/1962 | Beduhn et al. | 203/20 |
| 3,736,235 | 5/1973 | Sundquist | 202/185 A |
| 3,834,996 | 9/1974 | Aiso et al. | 203/8 |
| 3,887,425 | 6/1975 | Munch | 203/8 |
| 3,988,213 | 10/1976 | Yoshida et al. | 560/218 |
| 4,261,798 | 4/1981 | Palmer | 560/218 |

Primary Examiner—Wilbur L. Bascomb, Jr.
Attorney, Agent, or Firm—Sprung, Horn, Kramer & Woods

[57] ABSTRACT

A method and apparatus for distilling readily polymerizable liquid such as readily polymerizable monomers without causing the formation of an undesirable polymerization product is disclosed. This distillation is effected by
(a) vaporizing the polymerizable liquid from a liquid phase containing the same in an evaporator by externally heating the liquid phase;
(b) converting the vapor of the polymerizable liquid to a superheated state by externally heating, and introducing the vapor of the polymerizable liquid to the inlet of a condenser, while the vapor is maintained at the superheated state; and, then,
(c) condensing the vapor in the condenser, while a portion of the condensed fraction is circulated to the inlet of the condenser, whereby the condensation surface thereof is wetted.

3 Claims, 1 Drawing Figure

METHOD AND APPARATUS OF DISTILLATION FOR READILY POLYMERIZABLE LIQUID

The present invention relates to a method for industrially advantageously distilling readily polymerizable liquid and also relates to an apparatus therefor.

Distillation methods are conventionally used in the purification of the readily polymerizable liquid such as readily polymerizable monomers. For instance, U.S. Pat. Nos. 3,340,160 and 4,050,993 disclose the use of various polymerization inhibitors in the purification of the polymerizable liquid. U.S. Pat. Nos. 3,433,831 and 3,980,529 disclose the distillation of the polymerizable liquid under a reduced pressure or in vacuo to prevent the acceleration of the undesirable polymerization due to the increase in the temperature of the liquid. Furthermore, U.S. Pat. Nos. 3,781,193 and 3,980,529 propose the use of a so-called thin-layer type distillation method, in the purification of the polymerizable liquid, to prevent the undesirable polymerization due to the local heating of the liquid by lessening the temperature difference between the liquid and a heating source.

However, although these methods have solved the problems set forth in these patents, there are still the following problems in these methods. For instance, the methods in which polymerization inhibitors are used have the problem that, when the polymerization inhibitors are used in a vapor phase, the polymerization inhibitors are included in the purified products. Therefore, since various kinds of polymerization inhibitors should be used in accordance with the request of the users of the products, the operation becomes troublesome. The vacuum distillation is generally used in the distillation of readily polymerizable liquid to avoid the acceleration of undesirable polymerization due to the increase in the liquid temperature, since the boiling point of the liquid to be distilled is decreased under a vacuum pressure. However, since various kinds of readily polymerizable liquid have different polymerization characteristics from one another, appropriate pressure and temperature operation conditions cannot be necessarily selected with respect to the readily polymerizable liquid to be purified. In addition, the thin-layer type distillation method has the disadvantages that, when the polymerizable liquid contains solid matter and high-viscosity materials, the surface of the thin layer is likely to be contaminated and the cleaning thereof is troublesome.

Furthermore, since the polymerization of the evaporated vapor and the polymerization of the condensed liquid after the evaporation cannot be sufficiently prevented in each above-mentioned distillation method, these methods do not still satisfy the needs in the purification of the readily polymerizable liquid.

The important points of the distillation of the readily polymerizable liquid is that the distillation operation must be carried out in the presence of an appropriate polymerization inhibitor by using a simple distillation apparatus, especially, in such manners that the distillation temperature is as low as possible and that the distillation time is as short as possible. The undesirable polymerization products are mainly formed, during the distillation, at the dead spaces (i.e. liquid and vapor retention portions), the vapor-liquid contacting zones, the vapor phase zones in which the effect of the polymerization inhibitors is low and the like. The formation of the polymerization products in the apparatus during the distillation results in the clogging of the apparatus and the various problems in the distillation operation. In extreme cases, the apparatus is broken. Thus, it is important to prevent the formation of very small polymerization products in the distillation apparatus, since even very small polymerization products cause serious problems in the apparatus.

Accordingly, an object of the present invention is to obviate the above-mentioned problems and disadvantages in the conventional distillation of a readily polymerizable liquid and to provide a method and apparatus for industrially effectively distilling the readily polymerizable liquid without causing the formation of undesirable polymerization products.

Other objects and advantages of the present invention will be apparent from the description set forth hereinbelow.

In accordance with the present invention, there is provided a method for distilling readily polymerizable liquid comprising the steps of:

(a) vaporizing the polymerizable liquid from a liquid phase containing the same in an evaporator by externally heating the liquid phase;

(b) converting the vapor of the polymerizable liquid to a superheated state by externally heating, and introducing the vapor of the polymerizable liquid to the inlet of a condenser, while the vapor is maintained at the superheated state; and, then, (c) condensing the vapor in the condenser, while a portion of the condensed fraction is circulated to the inlet of the condenser, whereby the condensation surface thereof is wetted.

In accordance with the present invention, there is also provided an apparatus for distilling readily polymerizable liquid comprising:

(a) an evaporator provided with at least two external heating means which are located above and below the evaporating surface of the liquid to be evaporated therein;

(b) a condenser for condensing the evaporated vapor of the liquid;

(c) a conduit pipe provided with a heating means for connecting the evaporator and the condenser; and (d) a circulating means for circulating a portion of the condensed fraction in the condenser to the vapor inlet of the condenser, whereby the condensation surface of the condenser is wetted.

The present invention will be better understood from the description set forth below with reference to the accompanying drawing of FIG. 1 in which one typical embodiment of an apparatus for carrying out the distillation method according to the present invention is illustrated. However, it should be noted that the present invention is by no means limited to the embodiment illustrated in FIG. 1.

Referring to FIG. 1, an evaporator 10 is provided with an external heating means such as a heating jacket 11, whereby liquid 12 to be distilled contained in the evaporator 10 is externally heated. Into the inside of the heating jacket 11, a heating medium such as warm water, hot water, steam and the like is fed. Any conventional heating means such as a multi-pipe type or spiral-pipe type heater can also be used, together with the heating jacket 11. As illustrated in FIG. 1, the heating jacket 11 is mounted around the outer wall of the evaporator 11 in such a manner that the upper end 14 of the heating jacket 11 is always located above the liquid level 13 of the liquid 12 in the evaporator 10. Thus, the vapor-liquid contacting surface of the inner wall of the evaporator 10 is mildly heated and, therefore, the formation of undesirable polymerization products on the vapor-liquid contacting surface can be effectively prevented. Since the evaporated vapor and the condensed liquid thereof are generally present in the area above the evaporation surface and also since no polymerization inhibitor is generally contained in the evaporated vapor or the condensed liquid, undesirable polymerization products are formed in this portion if the vapor and liquid are excessively heated by a heating medium. Therefore, this zone should be mildly heated and the liquid level 13 of the liquid 12 to be distilled should be located lower than the upper end 14 of the heating jacket 11. Desirably, the vertical location of the upper end of the heating jacket 11 is at least 5 cm above the liquid level 13 of the liquid 12.

The evaporator 10 is also provided with a second external heating means such as a heating jacket 16, which is mounted around the outer wall of the evaporator 11 corresponding to a vapor zone 15 above the liquid evaporation surface 13 of the evaporator 10. Thus, the vapor evaporated from the liquid evaporation surface 13 is maintained at a superheated state and the condensation of the evaporated vapor on the inner wall of the vapor zone of the evaporator 10, which causes the formation of undesirable polymerization products on the inner wall in the absence of the polymerization inhibitor, can be effectively prevented. In FIG. 1, the heating medium can be separately passed through the heating jacket 11 and 16 by using an inlet and outlet 17 and 18, whereby the heating of the jacket 11 and the heating of the jacket 16 can be independently carried out. In addition, since it is desirable that the liquid 12 to be distilled in the evaporator 10 is uniformly heated during the distillation operation, an agitator 19 can be desirably installed in the evaporator. A level indicator 20 can also be conveniently attached to the evaporator 10.

The evaporator 10 is connected with a condensing means such as a condenser 22 through a conduit pipe 21, so that the vapor evaporated from the evaporator can be introduced into the condenser 22, while the vapor is maintained at a superheated state. The conduit pipe 21 is also equipped with an appropriate external heating means such as a heating jacket 23. The heating jacket 23 maintains the vapor evaporated from the evaporation surface 13 at a superheated state in order to prevent the condensation of the vapor on the inner wall of the conduit pipe 21, which causes the formation of the undesirable polymerization product on the inner wall of the connecting pipe 21. A heating medium having a given temperature can be passed through the heating jacket 23 via a heating inlet and outlet 24.

In the condenser 22, the vapor is cooled and condensed by an appropriate coolant. According to the present invention, a portion of a condensate 26 condensed in the condenser 22 is circulated from a condensate receiver 27 to the vapor inlet portion of the condenser 22, whereby the inner surface of condensation tubes 28 of the condenser 22 is wetted. Thus, the direct contact of the dry inner surfaces of the condensation tubes 28 with the superheated vapor, which causes the formation of undesirable polymerization products on the inner surface of the tubes 28, can be effectively prevented. The circulation of a portion of the condensate 26 is effected in such a manner that the inner surfaces of the condensation tubes 28 are entirely wetted. The circulation of the condensate 26 to the condensation tubes 28 can be effected by using any means which is capable of uniformly distributing the condensate 26 in the entire section of the flow paths of the condensation tubes 28. Examples of such uniform distribution means are conventional spraying means having one or more spray nozzles mounted on the top portion of the condenser 22 in such a manner that the condensate 26 can be uniformly distributed in the entire surface of the upper section of the condensation tubes 28. Otherwise, the uniform distribution of the circulating condensate can also be effected by placing a liquid reservoir on the upper end portion of the condensation tubes 28, whereby the condensate 26 contained in the reservoir is overflowed to the entire section of the condensation tubes 28. Consequently, a portion of the condensate 26 is circulated to the inlet of the condenser 22, so that the entire condensation surfaces of the condensation tubes 28 are wetted by the circulating liquid condensate and so that the amount of the circulated liquid, which is capable of forming and maintaining a liquid film on the condensation surface, is given.

It should be noted that a double-tube type or spiral plate type condenser can also be used, in lieu of the multi-tube type condenser 22, or otherwise a method in which a large amount of the cooled condensate is directly contacted with the vapor to liquefy the vapor can be used. Appropriate polymerization inhibitors can also be optionally included in the condensate 26.

It is desirable that the inner surface of the evaporator 10 is a smoothly finished surface and the formation of the possible gas retention portion (i.e. dead spaces) should be avoided as much as possible. For instance, as to a sight glass 29 and the like which should be inevitably attached to the evaporator 10, it is desirable that the length of the nozzle thereof is made as short as possible and the peripheral portion thereof is desirably heated with a jacket. It is also desirable that a heating fluid is internally flown through a pipe 30 installed within the shaft of an agitator 19, whereby the condensation of the vapor on the surfaces of the shaft and the blades is prevented and that the blades which are difficult to be heated is located at the lower section of the shaft in such a manner that the blades are dipped into the liquid to be evaporated so that the polymerization due to the adhesion of the condensate can be prevented.

The readily polymerizable liquids which can be advantageously distilled according to the present invention are those which are readily polymerizable upon heating. Examples of such liquids are: acrylic acid and methacrylic acid; acrylic acid alkyl esters and methacrylic acid alkyl esters such as methyl acrylate and methyl methacrylate, ethyl acrylate and ethyl methacrylate, butyl acrylates and butyl methacrylates, 2-ethylhexyl acrylate and 2-ethylhexyl methacrylate, lauryl acrylate and lauryl methacrylate, stearyl acrylate and stearyl methacrylate and the like; acrylic acid hydroxyalkyl esters and methacrylic acid hydroxyalkyl esters such as hydroxyethyl acrylates and hydroxyethyl methacrylates, hydroxypropyl acrylates and hydroxypropyl methacrylates and the like; acrylic acid dialkylaminoethyl esters and methacrylic acid dialkylaminoethyl esters such as dimethylaminoethyl acrylate and dimethylaminoethyl methacrylate, diethylaminoethyl acrylate diethylaminoethyl methacrylate and the like; glycidyl acrylate and glycidyl methacrylate; and other monomers such as acrylonitrile and methacrylonitrile, styrene, butadiene and the like.

The distillation of the readily polymerizable liquid is desirably carried out under a vacuum pressure as high as possible, so that the distillation can be effected at a low temperature, and by mild heating so that a large amount of heated water is passed through the heating jacket 11 so that the variability in the temperature of the heating medium in the entire heating surface can be lessened and also that the temperature of the laminar film at the boundary between the heating surface of the evaporator and the liquid to be evaporated can be lowered. For instance, in the case where 2-hydroxyethyl methacrylate is distilled, the distillation is desirably carried out under the conditions of the pressure of 3 through 7 Torr and the liquid temperature of approximately 70° C. through approximately 80° C. by using heated water having a temperature of 90° C. or less. Generally speaking, as exemplified above, the temperature of the heating medium in the heating jacket is desirably not more than approximately the actual boiling point of the liquid plus 20° C. As the heating medium, heated water, or saturated or wet steam is generally used and the use of superheated steam is not desirable.

It is important in the present invention that the evaporated vapor, after evaporation, should be maintained at a superheated state (or at a temperature higher than the dew point) so as not to be condensed until the vapor is introduced to the condenser 22. This is because, if the vapor is condensed on the vapor zone of the evaporator 10 or the inside of the conduit pipe 21, the undesirable formation of a polymerization product occurs in the inner wall surface of the evaporator 10 and the inner surface of the conduit pipe 21. For this reason, according to the present invention, the heating jacket are equipped around the vapor zone 15 of the evaporator 10 and the conduit pipe 21, so that the heating medium having a temperature higher than the dew point of the evaporated vapor is passed through the jacket. Thus, the evaporated vapor is maintained at a superheated state, whereby the condensation of the evaporated vapor on the inner surfaces of the evaporator 10 and the conduit pipe 21 can be prevented. Furthermore, in order to avoid the increase in the temperature of the liquid to be distilled due to the pressure loss derived from the vapor flow, the sectional structure of the vapor flow path is designed as large as possible, so that the vapor flow resistance becomes small. Thus, the vapor is desirably introduced to the condenser by way of a smooth path having no gas retention space.

In general, the temperature of the heating medium used in the heating jackets of the vapor zone of the evaporator 10 and the conduit pipe 21 is within the range of 5° C. plus the dew point of the evaporated vapor through 50° C. plus the dew point of the evaporated vapor under the system pressure. In the case where the temperature of the heating medium is less than 5° C. plus the dew point of the evaporated vapor, the local condensation of the evaporated vapor is likely to occur on the inner wall surfaces of the vapor zone of the evaporator 10 and the conduit pipe and, therefore, an undesirable polymerization product derived from the condensate is likely to be formed thereon. Contrary to this, the use of the temperature of the heating medium of more than 50° C. plus the dew point of the evaporated vapor is not desirable, because the heat energy required in the heating and condensation of the evaporated vapor becomes large and the thermal decomposition occurs depending upon the kind of the liquid to be distilled.

The superheated vapor introduced into the condenser is cooled and condensed on the condensation surface of the condenser. However, since the direct contact of the superheated vapor with the inner surface of the condensation tubes results in the formation of the gas-liquid boundary surface in the inner walls of the condensation tubes and polymerization rapidly occurs on this surface. Therefore, according to the present invention, a portion of the condensate is circulated to the inner wall surfaces of the condensation tubes to always maintain the inner wall surfaces of the condensation tubes under a wet state, whereby the vapor is cooled and condensed through the condensate liquid film on the inner wall surfaces of the condensation tubes. Furthermore, in the case where the condensate is sprayed, the superheated vapor is contacted with and cooled by the sprayed circulated condensate, prior to entrance to the condensation tubes, and the vapor actually introduced into the condensation tubes is converted from a superheated state to a vapor at the dew point containing partially condensed liquid. Therefore, the formation of the undesirable polymerization product can be effectively prevented and the condensation efficiency at the condensation tubes can be advantageously increased.

The present invention will now be further illustrated by, but is by no means limited to, the following Examples, in which all percentages are expressed on a weight basis unless otherwise specified.

EXAMPLE 1

Approximately 900 liters of 2-hydroxymethyl methacrylate synthetic reaction mixture obtained from the reaction of methacrylic acid with ethylene oxide in the presence of, as a catalyst, chromium acetate, were distilled by using a distillation apparatus as illustrated in FIG. 1.

The distillation apparatus was comprised of a 2000 liter evaporator (an inner wall surface being made of stainless steel SUS 304 and heating jackets being made of steel SS41) having an inner diameter of 1300 mm and a straight body length of 2000 mm connected, through a conduit pipe equipped with a heating jacket, with a vertical type multi-pipe condenser having a heat transfer surface of 15 m$^2$ and having tubes made of stainless steel SUS 304.

The 2-hydroxyethyl methacrylate synthetic reaction mixture containing 90% of 2-hydroxyethyl methacrylate and 10% of methacrylic acid, catalyst, a polymerization inhibitor, N,N-di-2-naphthyl-p-phenylenediamine and others was introduced into the evaporator. While the liquid was agitated with an agitator at 88 rpm so that the maximum liquid level in the evaporator was less than, by at least 20 cm, the top of the upper end of the lower heating jacket, a heating water having a controlled temperature of 90° C. was passed through the lower jacket. On the other hand, a saturated steam of 1 kg/cm$^2$ Abs. (having a saturated temperature of 100° C.) was passed through an upper jacket and also was passed through a jacket for the conduit pipe.

In order to prevent clogging in a liquid discharge at the bottom of the evaporator, nitrogen gas (air or other inert gases can also be used) was fed therefrom. Furthermore, in order to prevent the condensation of the vapor and the polymerization due to the liquid retention, a manhole was packed with packing and a liquid level indicator detecting portion was placed with elements, so that the inner wall surfaces around the manhole and the liquid level indicator detecting portions were smooth and the dead space in the agitator shaft attaching portion was made as small as possible. In addition, superheated vapor passed through the inside of the agitation shaft to prevent vapor condensation and polymerization due to liquid retention.

The pressure in the evaporator was controlled under 3 through 4 mm Hg by a vacuum pump 31 and the distillation was carried out at a liquid temperature of 80° C. The distillation rate was about 130 through 150 kg/H and the vapor phase temperature was 90° through 100° C.

The evaporated vapor was condensed in a condenser through the shell side of which condenser a coolant (20% aqueous methanol) having a temperature of 0° C. was passed. The condensed liquid was maintained at a temperature of 5° through 10° C. and 50 ppm of a polymerization inhibitor, hydroquinone monomethylether was added thereto. A portion (i.e. about 2000 kg/Hr) of the condensate was circulated to the inlet portion of the condenser and was uniformly sprayed over the upper end section of the condensation tubes by a spray nozzle.

Thus, purified 2-hydroxyethyl methacrylate was obtained, with no substantial formation of polymerization products, by distillation.

EXAMPLE 2

Approximately 900 liters of n-butylacrylate reaction mixture obtained from an ester interchange method, in which methyl acrylate was reacted with butanol in the presence of sulfuric acid as a catalyst were distilled by using the distillation apparatus used in Example 1. The n-butyl-acrylate reaction mixture, from which most of low boiling point components were previously removed, contained 92% of n-butyl acrylate and 8% of butanol, sulfuric acid, a polymerization inhibitor N,N'-di-2-naphthyl-p-phenylenediamine and other minor components.

While the liquid was agitated with an agitator at 88 rpm so that the maximum liquid level in the evaporator was less than, by at least 20 cm, the top of the upper end of a lower heating jacket, a heating water having a controlled temperature of 90° C. was passed through the lower jacket. On the other hand, a saturated steam of 2 kg/cm² absolute having a temperature of 120° C. was passed through an upper jacket and also was passed through a jacket for the conduit pipe. Various means for preventing clogging as used in the apparatus of Example 1 were also used in this Example.

The pressure in the evaporator was controlled under 35 through 40 mm Hg by a vacuum pump and the distillation was carried out at a liquid temperature of 80° C. or less. The distillation rate was 70 through 80 kg/H and the vapor phase temperature was 85° through 100° C.

The evaporated vapor was condensed in a condenser through the shell side of which condenser a coolant having a temperature of 0° C. was passed. The condensed liquid was maintained at a temperature of 5° through 10° C. and 50 ppm of hydroquinone monomethylether was added thereto. A portion of the condensate containing the polymerization inhibitor was circulated to the inlet portion of the condenser at a rate of about 2000 kg/H. The circulated condensate was uniformly sprayed over the upper end section of the condensation tubes by a spray nozzle. The distillation was continued for about 15 hours, while the circulation of the condensate was continued.

Thus, the purified n-butyl acrylate was obtained, with no substantial formation of a polymerization product, by distillation.

EXAMPLE 3

Four types of readily polymerizable liquid listed in Table 1 below were distilled under the conditions listed in Table 1 below.

Thus, the main component of each polymerizable liquid was obtained, with no substantial formation of a polymerization product, under the conditions listed in Table 1.

The composition of the liquid used in each Run, was as follows:

Run No. 1: 94% of 2-ethylhexyl acrylate and 6% of other components including octanol, sulfuric acid (catalyst), hydroquinone (polymerization inhibitor) and so on.

Run No. 2: 94% of n-butyl methacrylate and 6% of other components including butanol, sulfuric acid (catalyst), N,N'-di-2-naphthyl-p-phenylenediamine (polymerization inhibitor) and so on.

Run No. 3: 96% of dimethylaminoethyl methacrylate and 4% of the other components including dimethylaminoethanol, octyl tin oxide (catalyst), phenothiazine (polymerization inhibitor) and so on.

Run No. 4: 96% of 2-hydroxyethyl acrylate and 4% of other components including acrylic acid, chromium acetate (catalyst), N,N'-di-2-naphthyl-p-phenylenediamine (a polymerization inhibitor) and so on.

TABLE 1

| Run No. | Main Liquid Component | Heating Medium of Lower Heating Jacket | Heating Medium Temp. of Lower Heating Jacket | Liquid Temp. (°C.) | Evaporator Pressure (Torr) | Steam Pressure for Superheating (kg/cm²G) | Evaporated Vapor Temp. (°C.) | Condensate Circulating Flor rate (m³/Hr) | Condensate Temp. (°C.) |
| --- | --- | --- | --- | --- | --- | --- | --- | --- | --- |
| 1 | 2-Ethylhexyl Acrylate | Water | 90 | 75~80 | 8~10 | 0.5 | 90~100 | 2 | 4 |
| 2 | n-Butyl Methacrylate | Water | 90 | 75~80 | 5~6 | 0.5 | 85~95 | 2 | 4 |
| 3 | Dimethylaminoethyl Methacrylate | Water | 95 | 80~85 | 15~20 | 0.5 | 90~100 | 2 | 5 |
| 4 | 2-Hydroxyethyl Acrylate | Saturated Steam (0.9 kg/cm² Abs.) | 95 | 80~85 | 4~6 | 0.5 | 90~100 | 2 | 5 |

EXAMPLE 4

The distillation of Example 1 was repeated, except that the vapor phase temperature was decreased.

As a result, no formation of an undesirable polymerization product on the inner wall surface of the vapor phase zone of the evaporator was observed at a temperature of 78° C., which was higher than, by 5° C., the dew point (i.e. 73° C.) of 2-hydroxyethyl methacrylate under the system pressure (i.e. 3 Torr).

Furthermore, also in the case where the distillation of Example 2 was repeated, except that the vapor phase temperature was 82° C., which was higher than, by 5° C., the dew point (i.e. 77° C.) of n-butyl acrylate under the system pressure (i.e. 35 Torr), no formation of the polymerization product was observed.

EXAMPLE 5

The distillation of Example 1 was repeated, except that the temperature of the liquid heating medium was 93° C., which was higher than, by 20° C., the boiling point of the liquid to be distilled under the system pressure (3 Torr).

No formation of the polymerization product was observed in the evaporator.

COMPARATIVE EXAMPLE 1

The distillation of Example 1 was repeated, except that the liquid level of the liquid to be distilled was raised. In the case where the liquid level was reached at the approximate level of the upper end of the lower jacket, the polymerization product was built-up at the inner wall portion of the evaporator higher than, 10 through 20 cm, the liquid level in the evaporator.

We claim:

1. A method for distilling readily polymerizable liquid comprising the steps of:
    (a) vaporizing the polymerizable liquid from a liquid phase containing the same in an evaporator by externally heating the liquid phase with a heating medium having a temperature of not more than 20° C. above the boiling point of the polymerizable liquid under the system pressure while the polymerizable liquid and a vapor are separately heated by means of separate external heating means mounted on an outer wall of the evaporator, the vertical location of the upper end of the heating means for the polymerizable liquid being located above the liquid level of the polymerizable liquid in the evaporator;
    (b) superheating the vapor of the polymerizable liquid to a temperature from 5° to 50° C. above the dew point of the vapor under the system pressure by externally heating and introducing the vapor of the polymerizable liquid to the inlet of a condenser while the vapor is maintained in the superheated state; and, then,
    (c) condensing the vapor in the condenser, while a portion of a condensed fraction is circulated to the inlet of the condenser, whereby a condensation surface thereof is wetted.

2. A method as claimed in claim 1, wherein the vertical location of the upper end of the heating means for the polymerizable liquid is at least 5 cm above the liquid level of the polymerizable liquid in the evaporator.

3. An apparatus for distilling readily polymerizable liquid comprising:
    (a) an evaporator provided with at least two external heating means which are located so as to separately heat the polymerizable liquid and a vapor thereof in such manner that the vertical location of an upper end of the heating means for the polymerizable liquid is above the liquid level of the polymerizable liquid in the evaporator;
    (b) a condenser for condensing the evaporated vapor of the liquid;
    (c) a conduit pipe provided with a heating means for connecting the evaporator and the condenser; and
    (d) means for circulating a portion of a condensed fraction in the condenser to the vapor inlet of the condenser, whereby a condensation surface of the condenser can be wetted.

* * * * *